United States Patent
Brhel

(10) Patent No.: US 6,277,132 B1
(45) Date of Patent: Aug. 21, 2001

(54) NEEDLE INSERTER WITH A NEEDLE PROTECTION DEVICE

(75) Inventor: Klaus Brhel, Karlsruhe (DE)

(73) Assignee: Forschungszentrum Karlsruhe, GmbH, Karlsruhe (DE)

( * ) Notice: Subject to any disclaimer, the term of this patent is extended or adjusted under 35 U.S.C. 154(b) by 0 days.

(21) Appl. No.: 09/522,793

(22) Filed: Mar. 10, 2000

Related U.S. Application Data

(63) Continuation-in-part of application No. PCT/EP98/06090, filed on Sep. 24, 1998.

(30) Foreign Application Priority Data

Oct. 24, 1997 (DE) .............................................. 197 47 154

(51) Int. Cl.[7] .................................................... A61B 17/04
(52) U.S. Cl. ........................ 606/144; 206/63.3; 206/339; 206/340; 206/341
(58) Field of Search ................................... 606/139, 144; 206/63.3, 339–341

(56) References Cited

U.S. PATENT DOCUMENTS

| | | | |
|---|---|---|---|
| 5,571,090 | * 11/1996 | Sherts | 606/144 |
| 5,591,181 | 1/1991 | Stone et al. | 606/144 |
| 5,690,652 | * 11/1997 | Wurster | 606/144 |

* cited by examiner

*Primary Examiner*—Gary Jackson
(74) *Attorney, Agent, or Firm*—Klaus J. Bach

(57) ABSTRACT

In a needle inserter with a needle protector for surgical suturing instruments, including a needle insertion structure having a handle part at one end and a needle mounting part at the other end, a slot is disposed in a needle mounting part for engaging therein a suturing needle. Means are provided for placing the needle inserter onto a jaw of a suturing instrument such that the needle can be locked with the jaws of the suturing instrument, which then, upon compression of the handle part, can be removed. The protector, which is installed on the needle inserter by a manufacturer, holds the needle in its proper position in the needle inserter and covers the needle tip to prevent displacement of the needle and injuries to persons installing the needle in the suturing instrument.

5 Claims, 2 Drawing Sheets

NEEDLE INSERTER WITH A NEEDLE PROTECTION DEVICE

This is a continuation-in-part application of International application PCT/EP98/06090 filed Sep. 24, 1998 and claiming the priority of German application 197 47 154.4 filed Oct. 24, 1997.

BACKGROUND OF THE INVENTION

The invention relates to a needle insertion device with a needle protection device especially for surgical use.

Needle inserters are auxiliary devices used especially in surgery procedures to insert a needle into a suturing device including endoscopic suturing devices as well as conventional suturing devices used in open surgery. The insertion of a needle into a suturing device, however, is problematic since the needle is so short that it cannot be guided accurately by hand. In suturing devices with two jaws (see for example, U.S. Pat. No. 5,690,652), wherein the needle must be passed back and forth between the jaws, it must be originally accurately inserted into the needle holder of one of the two jaws.

Basically, there are two ways to solve this problem:

First, the needle could be taken out of a needle magazine and supplied to a grasping device by which the needle is then installed in the suturing instrument. In this case, the grasping device would be a re-useable device.

Second, the needle installation device is provided with a needle and is mounted for direct installation of the needle. After installation of the needle in the suturing instrument, the installation device is removed and discarded. It is not used again. Consequently, it must be inexpensive.

U.S. Pat. No. 5,591,181 discloses a needle insertion device with which a needle can be inserted into at least one branch of a pair of branches of a surgical suturing apparatus. The device comprises a body which supports the needle which is removably mounted therein. The body is so shaped that it can be placed at least on one of the two branches of the suturing apparatus in order to insert the needle.

It is the object of the present invention to provide a needle insertion device with which surgical needles, which are small and which cannot easily be handled, can be safely and reliably inserted into a surgical suturing instrument. The person attending to the procedure should be safe from piercing and scratching injuries by the needle when installing the needle.

SUMMARY OF THE INVENTION

In a needle inserter with a needle protector for surgical suturing instruments, including a needle insertion structure having a handle part at one end and a needle mounting part at the other end, a slot is provided in the needle mounting part for engaging therein a suturing needle. Means are provided for placing the needle inserter onto a jaw of a suturing instrument such that the needle can be locked with the jaws of the suturing instrument, which then, upon compression of the handles, can be removed. The protector, which is installed on the needle inserter by a manufacturer, holds the needle in its proper position in the needle inserter and covers the needle tip to prevent displacement of the needle and injuries to persons operating the suturing instrument.

The needle insertion device is supplied by the manufacturer as a fully assembled unit. The needle installation is automated such that the needle is accurately installed by the needle insertion device and is firmly engaged in the suturing device. After insertion of the needle in the inserter, the needle protector is moved with its T-shaped part onto the needle inserter up to a stop in which position the needle tip is covered by the needle protector. In this way, the needle itself is protected, since none of the two needle tips is exposed. Injuries to a person handling the needle, for example, upon removal from the packing are also prevented. The needle is received over much of its length in the insertion device in such a way that it is not released by an unintended compression of the handle area. Additionally, the two arms of the handle area may be held apart by a compression spring disposed there-between when the device is not used. Once the needle inserter is mounted onto the suturing instrument up to a final stop and the needle is engaged by the jaws of the suturing instrument, the needle inserter can be pulled off with a slight jerk when the two arms of the handle are pressed together. This can be achieved properly if the needle inserter consists of a plastic material, which is sufficiently firm but still elastic at normal ambient temperature. The needle inserter and the needle protection have a complicated surface so that their shape can be obtained easiest if they are manufactured by casting or by injection molding. Machining would be too expensive.

It is advantageous if the needle inserter and the needle protection are firmly interconnected by a string, and also if the needle is not simply released when the handle part is pressed together. Rather a slight jerk should be necessary to remove the needle from the needle inserter when the needle is installed in the suturing instrument. Preferably, the needle protection is inclined at the front end of the web adjacent the handle portion in accordance with the shape of the engaged by the needle inserter. The interconnection of the needle inserter and the needle protection by the string ensures that both parts are discarded together and none of the parts is unintentionally left unattended. This is particularly important for a single use article since both parts must be properly disposed of in order to avoid unnecessary cleaning.

Materials suitable for cleaning and sterilization in a medical sense are compounds such as PEEK, PE or TE.

The needle inserter with needle protection provides for always safe handling. If manufactured by casting or injection molding or other molding processes suitable for the material used, any desired amount of needle inserters can be manufactured perfectly and inexpensively. The needle is automatically mounted in the needle inserter already by the manufacturer and remains in place until it is installed in the suturing instrument. Even if the handle portion is unintentionally compressed, the needle still remains clamped in the needle inserter as long as no other forces are applied.

The packaged needle inserter including needle protection is shown in the drawings and will be described below in detail.

DESCRIPTION OF A PREFERRED EMBODIMENT

The needle inserter 1 as well as the needle protection 2 are injection molded and consist of the same material, which is polyethylene (PE). They may also be formed by casting in a mold. The edges are rounded already in the molding process so that, after the molding step, no additional manufacturing step is required.

Figure 1A:
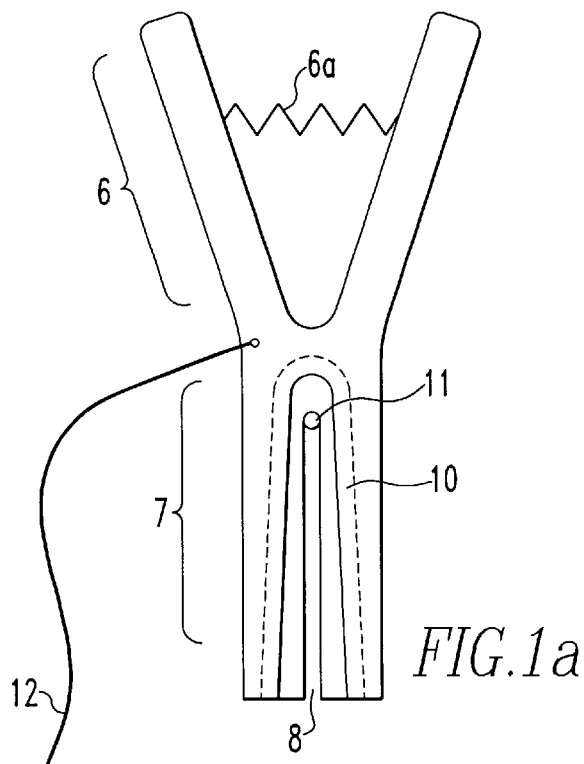
FIG. 1a is a side view of the needle inserter.
Figure 1B:
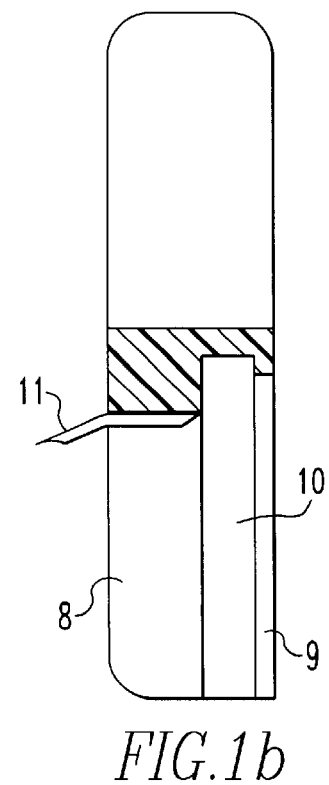
FIG. 1b is a cross-sectional view of the needle inserter shown in FIG. 1a, FIGS. 2a and 2b show the needle protection in the proper positions respective to FIGS. 1a and 1b for placement onto the needle inserter, and, FIGS. 3a, 3b, 3c, 3d, 3e and 3f illustrate in steps the procedure of installing a suturing needle in a suturing instrument using the needle inserter according to the invention.

FIG. 1a shows the needle inserter 1 with its clothesline pin configuration including a handle part 6 and its mounting part 7 with the intermediate pivot joint structure. The pivot joint structure acts as a joint because of the property of the material of which the needle inserter 1 consists. However, in no position of the handle portion, even if compressed, is the clamping effect holding the needle 11 completely eliminated. A compression spring 6a may be disposed between the handles of the handle structure to increase the engagement forces. The needle inserter 1 has a distal end with a first longitudinal slot 8 formed into a thick wall portion of the needle inserter, wherein the needle 11 can be frictionally engaged so as to be firmly held in position at the longitudinally inner end of the slot 8. The second slot 9 extends parallel to the slot 8 and has a slight wedge shape whereby the needle is guided when it is inserted over a jaw of the suturing instrument. Between the slots 8 and 9, there is a groove 10, which has a contour parallel to that of the slot 9. The groove 10 and the slot 9 are so formed that the needle inserter 1 can be fully pushed onto the movable jaw of the suturing instrument. The needle 11 is disposed at the inner end of the slot 8, where it is engaged between the side walls of the slot 8 and also between the end 5a of the wall portion 5b of the needle protector 2 and the curved end wall of the slot 8. In this way, the needle 11 is firmly held in a position in which the opposite needle points can be received in the respective retaining openings of the jaws of the suturing instrument when the needle inserter is in place on the movable jaw of the suturing instrument. In FIG. 1b, the U-shaped end of the slot extends at an angle of 90° with respect to the longitudinal axis of the needle inserter. The joint area is shown cut, with one of the arms removed so that the position of the needle 11 is clearly visible. It is noted that the U-shaped end wall may be inclined with respect to the longitudinal axis of the needle-depending on the shape of the needle.

Figure 2A:
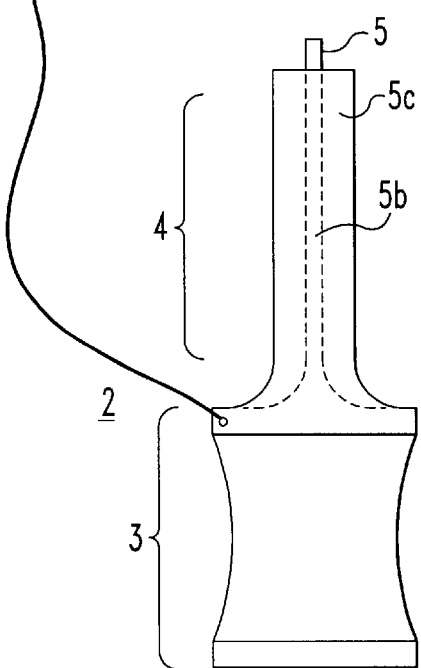
Figure 2B:
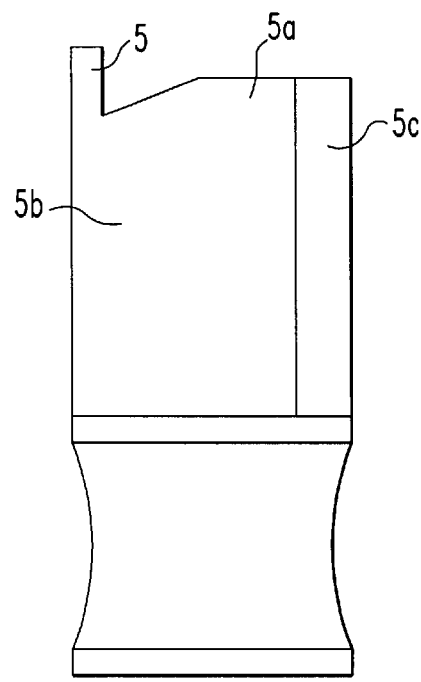
Figure 3F:
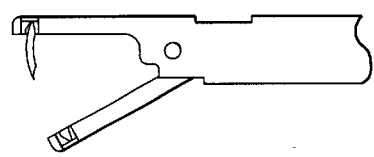
Figure 3E:
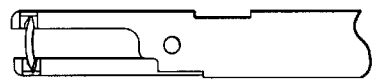
Figure 3D:
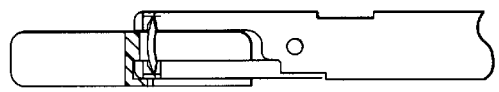
Figure 3C:
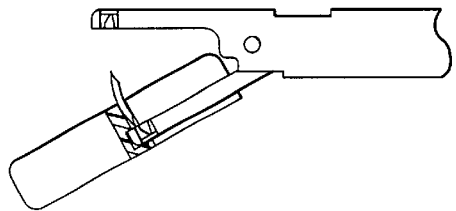
Figure 3B:
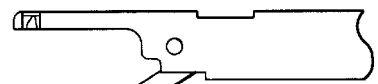
Figure 3A:
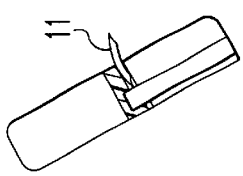

FIGS. 2a and 2b show the needle protector 2 with a grasping end 3 in its position with respect to FIGs. 1a and 1b such that it can be placed onto the needle inserter 1. The web 5b of the T-shaped part 4 of the protector is then disposed in the slot 8 and the foot portion 5c is disposed in the groove 10. The projection 5 of the web 5b extends over the tip of the needle 11 so as to cover the needle tip and prevent injuries from the needle tip.

FIGS. 3a to 3f show the various phases of inserting the needle 11:

3a) The needle inserter 1 with the needle 11 and needle protector 2 disposed on the needle inserter 1 are removed from a sterile packing in which they are supplied by a manufacturer. The movable jaw of the suturing instrument shown underneath the protected needle inserter is fully open.

3b) The needle protector 2 is removed from the needle inserter 1. The needle tip covered so far is exposed. The needle inserter 1 with the needle 11 disposed thereon is placed into insert position for sliding the needle inserter onto the movable jaw.

3c) The needle inserter is pushed onto the movable jaw, which is generally slightly wedge-shaped, until it abuts the end of the insertion path. The movable jaw is received in the groove 10 for guidance. When fully inserted, the needle inserter is in engagement with the movable jaw and is properly positioned in a position in which the needle 11 can be transferred to the jaws of the suturing instrument.

3d) The movable jaw is pivoted toward the stationary jaw such that both needle tips are received and engaged in the respective receivers of the two jaws of the suturing instrument.

3e) The handle portion 6 of the insert device is now compressed whereby the engagement forces for the needle are reduced. The needle inserter is pulled out with a slight jerk. The needle remains engaged between the two jaws of the suturing instrument.

3f) The needle 11 is locked in the stationary jaw of the suturing instrument by actuation means of the operating handle of the suturing instrument. The movable jaw is pivoted open. The suturing instrument is ready for suturing.

The needle is disposed on a circle having its centerpoint on the pivot axis of the movable jaw. The needle should therefore be curved in accordance with the curvature of the circle or at least it should be bent in the center to approximate the curvature of the circle.

Basically, the installation of the needle can be performed also on the stationary jaw. However, since the movable jaw is generally smaller, also the needle inserter can be smaller if it is designed for the smaller jaw. If both jaws are pivotable, the needle inserter can be designed for use with either jaw.

In order to reduce the demands on the surgery personnel and for safety reasons, it is advantageous, if both parts, the needle inserter and the needle protector, are interconnected by a string 12 already in the factory. In this way, the two parts are interconnected also after the installation of the needle in the suturing instrument. If these parts are then discarded, since they are single use parts, it is made sure that both parts are properly discarded.

What is claimed is:

1. A needle inserter with a needle protector for surgical suturing instruments, comprising:

a needle insertion structure having a clothesline clip-like handle part at one end and a mounting part at the opposite end, said mounting part having longitudinal slots with an internal groove disposed therebetween, one of said slots, that is the walls defining said one slot, having a curved end and a predetermined width corresponding to the space between two jaws of a suturing instrument when disposed in a parallel closed position, and the other of said slots and said internal groove being wedge-shaped so that said needle inserter can be pushed fully onto a correspondingly shaped jaw of said suturing instrument, a suturing needle received, and engaged in, said one slot so as to be disposed at the curved end thereof in a predetermined position, a needle protector with a grasping end and a T-shaped front part with a web adapted to be received in said one slot and having an end with an extension projecting over the tip of a suturing needle disposed in said needle insertion structure when said needle protector is in place on said needle insertion structure, said web, said protector and said needle inserter consisting of an elastic plastic material, which permits the parts to be molded and which also permits resilient engagement of said needle in said first slot, but permits removal of said needle when said handle part of said needle inserter is compressed.

2. A needle inserter according to claim 1, wherein said needle insertion structure and said needle protector are interconnected by a string.

3. A needle inserter according to claim 2, wherein the engagement of said needle in said slot is sufficiently strong so that the needle will not fall out of said slot when said handles are compressed but that, with the handles compressed, a predetermined force is needed to remove the needle insertion structure from the needle when the needle is installed in a suturing instrument.

4. A needle inserter according to claim 3, wherein said needle protector web has, adjacent said projection, a section which is inclined toward said handle portion in adaptation to a bent end part of a suturing needle.

5. A needle inserter according to claim 4, wherein a compression spring is disposed between the two handles of said needle insert structure.

* * * * *